United States Patent [19]
Bachman et al.

[11] 4,022,057
[45] May 10, 1977

[54] EXPANDING TOOL FOR NONDESTRUCTIVE INSPECTION OF FLEXIBLE WIRE ROPE

[75] Inventors: John L. Bachman, Taneytown, Md.; Joseph M. Krafft, Alexandria, Va.

[73] Assignee: The United States of America as represented by the Secretary of the Navy, Washington, D.C.

[22] Filed: July 12, 1976

[21] Appl. No.: 704,155

[52] U.S. Cl. .................................. 73/99; 73/103
[51] Int. Cl.² .......................................... G01N 3/26
[58] Field of Search ....................... 73/99, 103, 158

[56] References Cited
UNITED STATES PATENTS
3,028,720  4/1962  Houk ........................... 73/103 X

*Primary Examiner*—Jerry W. Myracle
*Attorney, Agent, or Firm*—R. S. Sciascia; Philip Schneider; Melvin L. Crane

[57] ABSTRACT

A tool for nondestructive testing of wire rope. Wire rope is held in position in a frame by two grips such as gripper pliers. One grip is rotated relative to the other thereby reverse-twisting and opening the rope strands. Visual observation will reveal any damaged strand wires. The device is provided with mechanical stops to prevent over-twisting which may damage the wire rope.

3 Claims, 2 Drawing Figures

EXPANDING TOOL FOR NONDESTRUCTIVE INSPECTION OF FLEXIBLE WIRE ROPE

BACKGROUND OF THE INVENTION

This invention relates to fatigue testing of wire rope and more particularly to a device for reverse-twisting the strands for a non-destructive visual observation.

Heretofore various methods have been tried for determining damage to a wire rope cable. One method is a magnetic perturbation test for elevator cables. This is successful if properly used; however, the equipment is very expensive and complex. X-ray inspection and other methods have been used without success.

SUMMARY OF THE INVENTION

This invention is a simple device which makes use of two gripper pliers which are so assembled relative to each other that the wire strands of a twisted cable may be back-twisted for visual observation. The device is inexpensive, it is small and may be used in the "field" as well as in a workshop.

DETAILED DESCRIPTION

Figure 1:
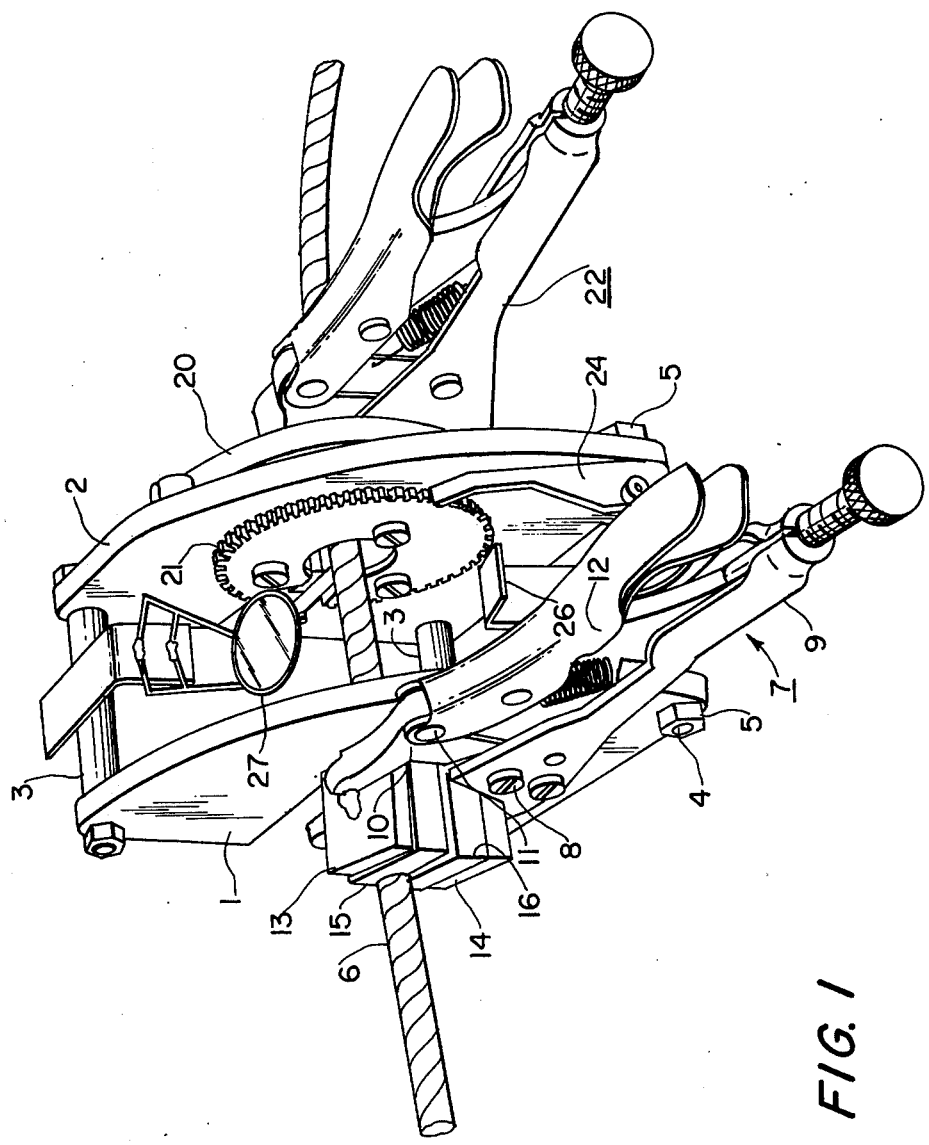
FIG. 1 illustrates a side and back view in perspective which illustrates the relative parts.
Figure 2:
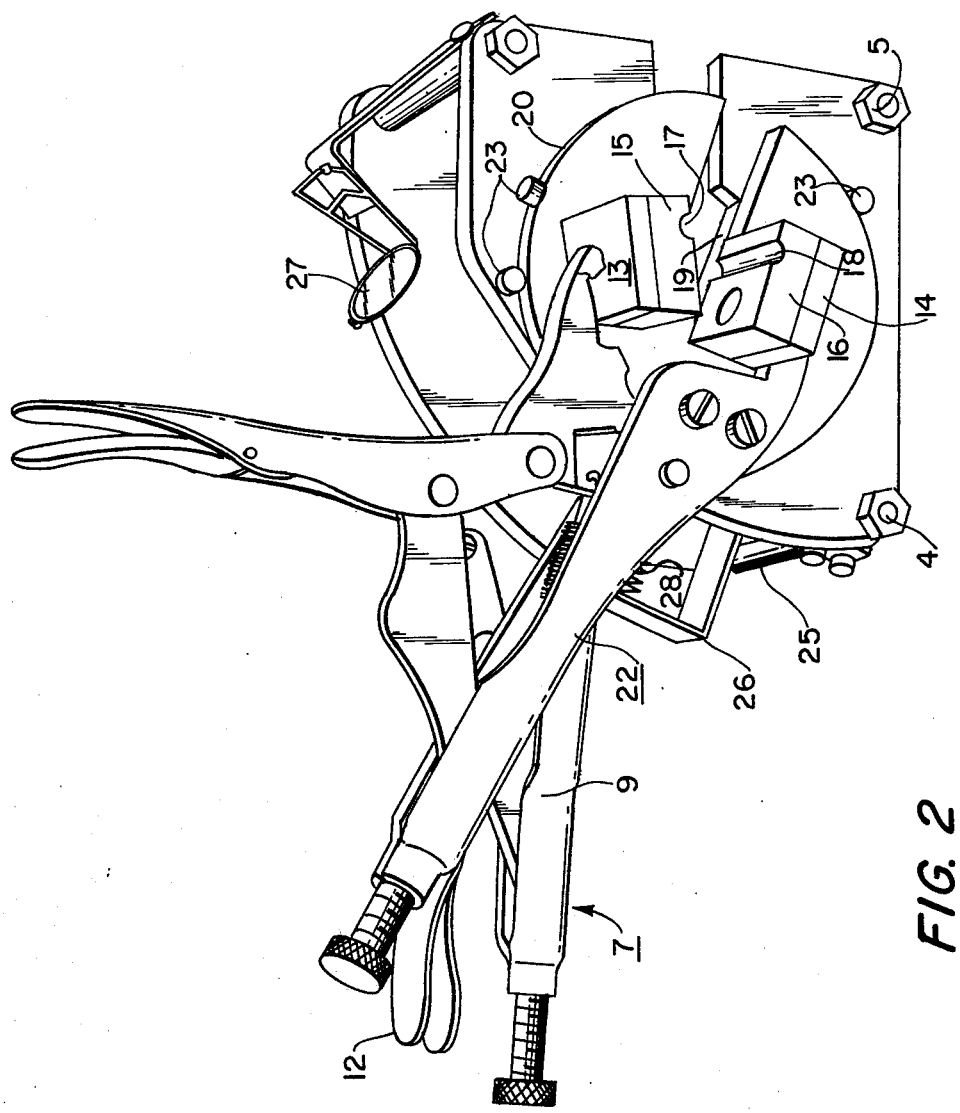
FIG. 2 is a side view from the side opposite to that of FIG. 1.

Now referring to the drawing, there is shown by illustration a flexible-wire-rope, nondestructive inspection device. As shown, the device includes a frame formed by end plates 1 and 2 separated by sleeves 3 which are held in place by threaded rods 4 and nuts 5 threaded onto each end of the rods. Each of the plates is provided with a slot that extends from the front to the mid-region substantially in a horizontal plane. The slot has sufficient height for the insertion or reception of a wire rope of the size to be tested.

A toggle-locking plier 7 is secured to the outer face of end plate 1 by suitable screws or bolts 8 which anchor or secure the arm 9 in a stationary position with the upper part of the bottom jaw even with the lower surface of the slot. The movable jaw of the plier is pivotable about pivot 11 when actuated by the conventional toggle mechanism and the movable handle 12. To aid in gripping the wire rope without damage thereto and for obtaining a firm grip, the jaw of the plier is modified to include an upper metal plate 13 and a lower metal plate 14. The upper and lower plates are provided with a suitable liner such as a resilient plastic pad 15,16. Each pad is provided with a suitable semicylindrical groove 17,18 across its face so that the groove is in alignment with the inner face of the slot in the plates. The diameter of the groove in the pads should be just slightly less than that of the rope to be tested. The resilient plastic pads are held in place on the metal plates 13 and 14 by suitable screws and are interchangeable to provide pads with differentdiametric grooves for different-diameter rope.

A second toggle-locking plier 22 is secured to a turntable relative to end plate 2 on the outside thereof. The end plate 2 is bored out to serve as a journal bearing for the turntable. The turntable is made into two parts, a platter 20 and a collar 21. The platter comprises a largediameter disc and a smaller-diameter boss 19 whose diameter is slightly less than the diameter of the journal bearing. The collar is secured to the boss by screws so that the collar rotates with the boss. The thickness of the boss is slightly larger than that of the end plate 2 so that the platter and collar may be rotated relative to the end plate 2 as the boss rotates within the journal bearing.

The platter 20 and collar 21 are slotted with the slot extending to its mid-region to match the slot in the end plate 2. The second plier is secured to the platter by suitable screws such that the bottom jaw with the metal plate 14 and resilient plastic pad will align with the bottom face of the slot in the platter. The grooves 17 and 18 are so positioned that they align with the grooves 17,18 in the pad on the first plier. The grooves, slots, and jaws are so aligned that the wire rope held in place by the jaws will be substantially perpendicular to the end plates. The platter and the end plate are provided with stops 23 so that when one stop on the plate and the stop on the platter are in contact, the slots in the end plates, the collar, and the platter will be in alignment. A second stop 23 is provided on the end plate to limit the rotation of the second plier relative to the first plier so that a wire rope held by the two pliers will be rotated only through a certain amount of degrees of rotation to prevent damage to the rope.

The collar is provided with teeth on its outer surface so that a pawl 24 cooperating therewith will hold the turntable in a desired position against return to its starting position until released. The pawl is journaled about the rear-spacer 3 and released by a depressing lever 26 which is connected with the pawl 24. A spring 28 secured to the depressing lever applies tension on the pawl to hold it against the collar until released by depressing the lever 26.

A magnifying glass 27 may be held in place by the upper-front spacer 3 in order to view the wire under magnification.

In operation, with a free-ended wire rope, the wire rope is inserted through the aligned slots with the twist toward the handle and the jaws of the toggle-locking pliers in the open position. The jaws of the pliers are closed to clamp the wire rope in place. The pliers secured to the the turntable is rotated upwardly while holding the stationary pliers in its fixed position. As the pliers 22 is rotated, holding the rope in place, the wire twists are untwisted. As the wires are untwisted the inner wires will be exposed and they can be examined visually. The magnifying glass may be used for better observation. If the wire is not free-ended, sufficient slack must be in the wire on each side of the pliers to permit rotation of the wire so that the parts of the wire on the outside of the clamped jaws will not be untwisted. Also, there should be no load on the wire when checked. Of course, if the wire is not free, the twisting device is placed onto the wire at the desired position for testing and the above procedure is followed.

When internal breaks exist, it has been determined that the broken wires in the outer strands become partially unwound and loosened from their strand positions and are thus obvious to the eye. When the rope is intact, the twisting birdcages the outer strands sufficiently to permit visual inspection of the (internal wire rope core) and underside of outer strands, either directly or with slight magnification using the glass 27 provided, and a local illuminator. Even if wires are broken, the rope will restore itself to its original layup when the pliers are reset and released.

The limits of benign rotation will depend on the character of the rope tested. As an example, 1/4 inch diameter, 7 × 19 improved plow steel wire rope with an internal wire rope core, a reverse twist of 135° in ten diameters (2½ inches) of test was found permissible, yet adequate for the test. Whether or not the reverse twisting is truly harmless to good cable, hence "non-destructive", is still under investigation. It is presumed that the release of internal breaks in a partially fatigued rope would hasten its failure, but in such cases, the cable should be replaced at once.

Obviously many modifications and variations of the present invention are possible in light of the above teachings. It is therefore to be understood that within the scope of the appended claims the invention may be practiced otherwise than as specifically described.

What is claimed and desired to be secured by Letters Patent of the United States is:

1. A tool for non-destructive testing of flexible wire rope which comprises:
    first and second gripper pliers secured relative to each other,
    said first gripper plier fixed against rotation,
    said second gripper plier rotatable relative to said first gripper plier,
    whereby a portion of a wire cable held between the jaws of said first and second gripper pliers may be untwisted by rotation of said second pliers relative to said first pliers for a visual observation of the innermost wires.

2. A tool for non-destructive testing of flexible wire rope as claimed in claim 1 which includes:
    mechanical stop means to limit the rotation of said rotatable plier relative to said fixed plier to avoid damage to the wire rope during untwisting.

3. A tool for non-destructive testing of flexible wire rope as claimed in claim 2 which comprises:
    first and second end plates secured relative to each other and held apart by equi-spacers,
    said end plates including a slot therein in the same plane and extending from the front to the mid-region,
    said first gripper pliers secured to the outside surface of said first plate with its bottom jaw along the bottom of the slot in said first end plate,
    said second en plate including a journal bearing with the axis at its mid-region,
    a rountable secured relative to said second end plate and including a slot therein;
    said roundtable including a platter on the outside surface of said second end plate and a collar on the inside surface of said second end plate,
    said platter including a large-diameter disc along the outside surface of said second end plate and a smalldiameter cylindrical boss journaled within said journal bearing, and
    said second plier being secured to said roundtable with the lower jaw of said second plier along the slot in said roundtable for rotation with said roundtable relative to said second end plate.

* * * * *